(12) United States Patent
Lee et al.

(10) Patent No.: US 9,377,418 B2
(45) Date of Patent: Jun. 28, 2016

(54) X-RAY IMAGING APPARATUS AND X-RAY IMAGING METHOD

(71) Applicant: SAMSUNG ELECTRONICS CO., LTD., Suwon-si (KR)

(72) Inventors: Jong Ha Lee, Hwaseong-si (KR); Kang Ho Lee, Hwaseong-si (KR); Young Hun Sung, Hwaseong-si (KR); Sang Wook Han, Busan (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 246 days.

(21) Appl. No.: 14/132,522

(22) Filed: Dec. 18, 2013

(65) Prior Publication Data
US 2014/0185762 A1 Jul. 3, 2014

(30) Foreign Application Priority Data

Jan. 3, 2013 (KR) .......................... 10-2013-0000501

(51) Int. Cl.
*G01N 23/04* (2006.01)
*A61B 6/00* (2006.01)
*H04N 5/32* (2006.01)

(52) U.S. Cl.
CPC *G01N 23/04* (2013.01); *A61B 6/42* (2013.01); *A61B 6/4233* (2013.01); *A61B 6/502* (2013.01); *A61B 6/54* (2013.01); *A61B 6/544* (2013.01); *A61B 6/545* (2013.01); *A61B 6/585* (2013.01); *H04N 5/32* (2013.01)

(58) Field of Classification Search
CPC ........ A61B 6/4233; A61B 6/585; A61B 6/42; A61B 6/502; A61B 6/54; A61B 6/544; A61B 6/545; G01N 23/04; H04N 5/32
USPC ..................................................... 378/37, 62
See application file for complete search history.

(56) References Cited

U.S. PATENT DOCUMENTS

| 7,138,636 | B2 | 11/2006 | Petrick et al. |
| 7,639,779 | B2 | 12/2009 | Kashiwagi et al. |
| 2005/0111617 | A1 | 5/2005 | Shoji |
| 2012/0199750 | A1* | 8/2012 | Kondou ................... H04N 5/32 |
| | | | 250/370.09 |

FOREIGN PATENT DOCUMENTS

| FR | 2 959 320 A1 | 6/2014 |
| JP | 2006-334154 A | 12/2006 |
| JP | 2007-215868 A | 8/2007 |
| WO | 2007/034033 A1 | 3/2007 |

OTHER PUBLICATIONS

Communication dated Jun. 23, 2014 issued by the European Patent Office in counterpart European Application No. 14150067.8.

* cited by examiner

*Primary Examiner* — Courtney Thomas
(74) *Attorney, Agent, or Firm* — Sughrue Mion, PLLC

(57) ABSTRACT

An X-ray imaging apparatus includes an X-ray generator configured to generate and radiate X-rays to a subject, an X-ray detector configured to detect and convert X-rays transmitted through the subject into an image signal, and a controller configured to analyze the image signal of the subject and set gain of the X-ray detector according to detection regions.

27 Claims, 17 Drawing Sheets

X-RAY IMAGING APPARATUS AND X-RAY IMAGING METHOD

CROSS-REFERENCE TO RELATED APPLICATION

This application claims priority from Korean Patent Application No. 10-2013-0000501, filed on Jan. 3, 2013, in the Korean Intellectual Property Office, the disclosure of which is incorporated herein in its entirety by reference.

BACKGROUND

1. Field

Apparatuses and methods consistent with exemplary embodiments relate to an X-ray imaging apparatus to transmit X-rays through a subject to generate an X-ray image and an X-ray imaging method.

2. Description of the Related Art

An X-ray imaging apparatus radiates X-rays to a subject, analyzes X-rays transmitted through the subject, and checks an internal structure of the subject. Since transmission of X-rays varies according to properties of materials configuring the subject, the internal structure of the subject may be imaged by detecting X-ray flux through the subject.

When auto exposure control (AEC) is performed, pre-shot of the subject may be analyzed to calculate X-ray imaging conditions optimized according to the properties of the subject and then main shot may be performed based on the calculated imaging conditions.

However, in the AEC, the optimized imaging conditions are equally set with respect to an entire image based on a specific intensity level of an entire region or a predetermined region of a pre-shot image. Therefore, an intensity level may be reduced or saturated according to density, thickness or attenuation properties of each region of the subject. Thus, accurate information may not be obtained for each of regions of the subject.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more exemplary embodiments provide an X-ray imaging apparatus to control sensitivity or gain upon X-ray detection according to regions of a subject based on thickness, density or X-ray attenuation properties of the subject to provide higher dynamic range images corresponding to various thicknesses, densities or X-ray attenuation properties per image, and an X-ray imaging method for the same.

Additional aspects will be set forth in part in the description which follows and, in part, will be obvious from the description, or may be learned by practice.

In accordance with an aspect of an exemplary embodiment, there is provided an X-ray imaging apparatus including an X-ray generator configured to generate and radiate X-rays to a subject, an X-ray detector configured to detect and convert X-rays transmitted through the subject into an image signal, and a controller configured to analyze the image signals of the subject and set the gain of the X-ray detector according to detection regions.

The X-ray detector may include a plurality of pixel regions and each detection region of the X-ray detector includes at least one pixel region.

The controller may analyze the image signal of the subject and extract a noise region and a saturation region from the image signal.

The controller may determine a detection region, a level of an image signal of which is equal to or greater than a first reference level, among the detection regions of the X-ray detector as the saturation region and determine a detection region, a level of an image signal of which is equal to or less than a second reference level, among the detection regions of the X-ray detector as the noise region.

The controller may set a value higher than original gain as gain with respect to the noise region of the X-ray detector and set a value lower than the original gain as gain with respect to the saturation region of the X-ray detector, wherein the original gain is gain of the X-ray detector applied when the analyzed image signal is obtained.

The controller may set a value higher than original gain as gain with respect to a detection region, the level of an image signal of which is equal to or greater than the first reference level, among the detection regions of the X-ray detector and set a value lower than the original gain as gain with respect to the detection region, the level of an image signal of which is equal to or less than the second reference level, among the detection regions of the X-ray detector.

The controller may set offset according to the detection regions of the X-ray detector.

The X-ray detector may include an amplifier configured to amplify the converted electrical signal and a gain control circuit configured to receive the gain set by the controller and control the gain of the amplifier.

The X-ray detector may further include an offset control circuit configured to receive offset set by the controller and control offset of the X-ray detector.

The X-ray generator may radiate X-rays to the subject in pre-shot, and the image signal analyzed by the controller may be an image signal converted from X-rays transmitted through the subject in the pre-shot.

The X-ray detector may control the gain of the detection region according to the gain set by the controller, convert X-rays transmitted through the subject in main shot into an image signal, and amplify and output the image signal according to the controlled gain.

The X-ray detector may control the gain of the detection region according to the gain set by the controller and amplify and output the converted image signal again according to the controlled gain.

In accordance with an aspect of another exemplary embodiment, there is provided a method of generating an X-ray image including generating and radiating X-rays to a subject, detecting and converting X-rays transmitted through the subject into an image signal, and analyzing the image signal of the subject and setting gain of an X-ray detector according to detection regions of the X-ray detector.

The X-ray detector may include a plurality of pixel regions and each detection region of the X-ray detector may include at least one pixel region.

The analyzing the image signal of the subject may include analyzing the image signal of the subject and extracting a noise region and a saturation region from the image signal.

The analyzing the image signal of the subject may include determining a detection region, a level of an image signal of which is equal to or greater than a first reference level, among the detection regions of the X-ray detector as the saturation region and determining a detection region, a level of an image signal of which is equal to or less than a second reference level, among the detection regions of the X-ray detector as the noise region.

The setting the gain of the X-ray detector according to detection regions may include setting a value higher than original gain as gain with respect to the noise region of the X-ray detector and setting a value lower than the original gain as gain with respect to the saturation region of the X-ray detector, wherein the original gain is gain of the X-ray detector applied when the analyzed image signal is obtained.

The analyzing the image signal of the subject and setting the gain of the X-ray detector according to detection regions may include setting a value higher than original gain as gain with respect to a detection region, the level of an image signal of which is equal to or greater than the first reference level, among the detection regions of the X-ray detector and setting a value lower than the original gain as gain with respect to a detection region, the level of an image signal of which is equal to or less than the second reference level, among the detection regions of the X-ray detector.

The method may further include setting offset according to the detection regions of the X-ray detector.

The analyzed image signal of the subject may be an image signal converted from X-rays transmitted through the subject upon pre-shot.

According to an aspect of still another exemplary embodiment, there is provided an X-ray detector of an X-ray imaging apparatus which provides an X-ray image of a subject including a plurality of detection regions configured to detect and convert X-rays transmitted through the subject into an electrical signal, wherein a detection region comprises an amplifier configured to amplify a converted electrical signal of an X-ray, wherein gain of the amplifier is determined based on comparison between a level of the converted electrical signal with a predetermined reference level.

According to an aspect of still another exemplary embodiment, there is provided an X-ray imaging apparatus including an X-ray source; an X-ray detector including a plurality of detection regions and configured to detect an X-ray intensity of an X-ray passing through a subject; and a controller configured to control gain of the X-ray detector based on the detected X-ray intensity according to each of the plurality of detection regions.

BRIEF DESCRIPTION OF THE DRAWINGS

The above and/or other aspects will become more apparent by describing certain exemplary embodiments with reference to the accompanied drawings in which.

DETAILED DESCRIPTION

Hereinafter, an X-ray imaging apparatus and a method of controlling an X-ray imaging apparatus according to exemplary embodiments will be described with reference to the accompanying drawings.

Figure 1:
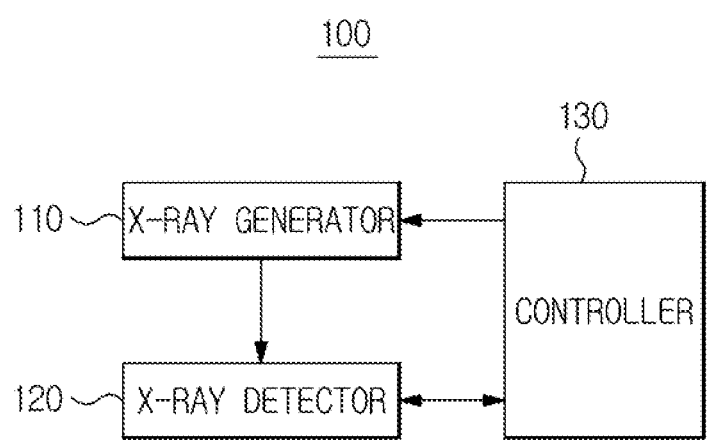
FIG. 1 is a block diagram showing an X-ray imaging apparatus according to an exemplary embodiment.
Figure 2:
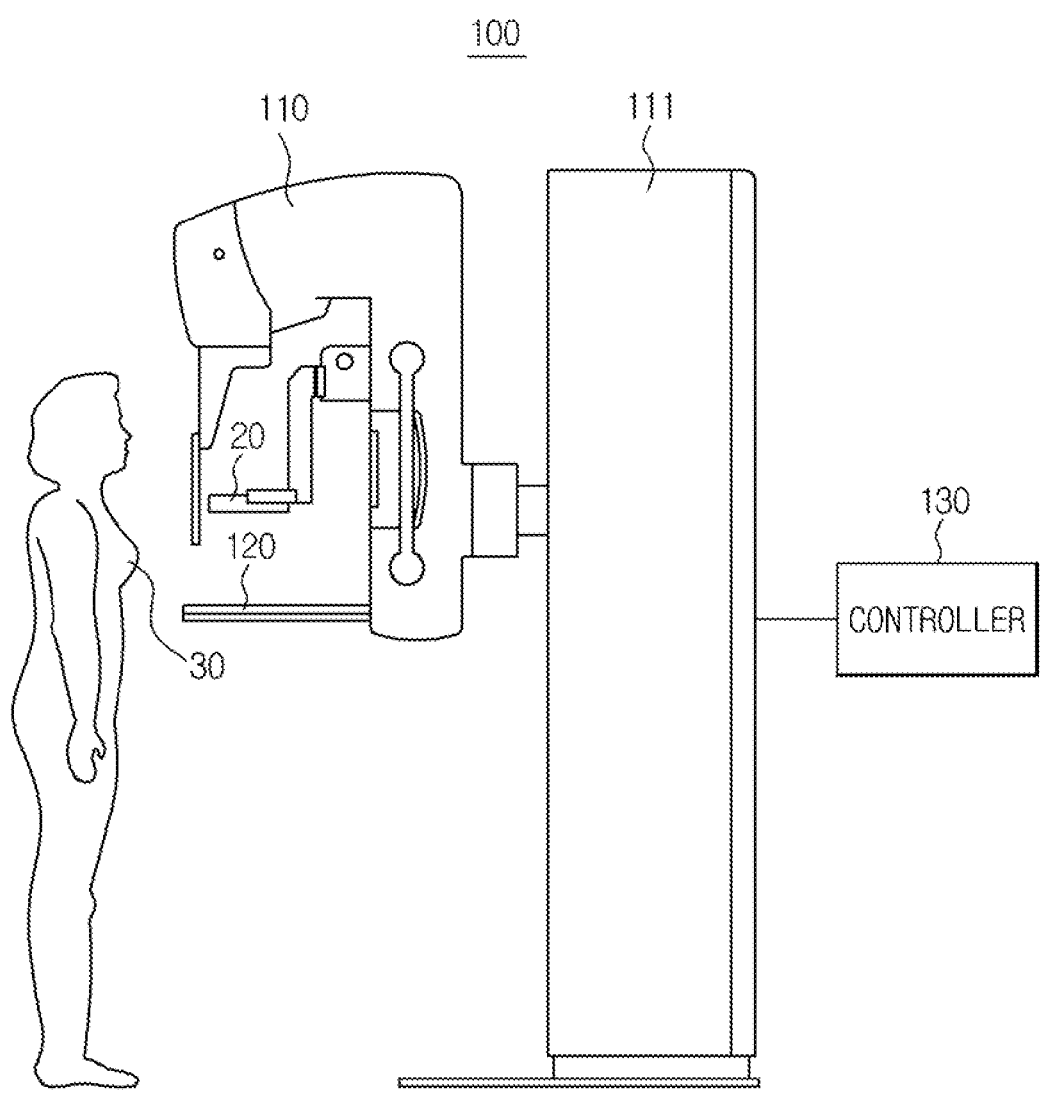
FIG. 2 is a schematic diagram showing an X-ray imaging apparatus for mammography.

FIG. 1 is a block diagram showing an X-ray imaging apparatus according to an exemplary embodiment, and FIG. 2 is a schematic diagram showing an X-ray imaging apparatus for mammography.

A structure or control conditions of an X-ray imaging apparatus 100 according to an exemplary embodiment may be changed according to a subject to be imaged. Although a subject to be imaged by the X-ray imaging apparatus 100 is not limited, an X-ray imaging apparatus for mammography is shown in FIG. 2 as an exemplary application of the X-ray imaging apparatus 100.

Referring to FIGS. 1 and 2, the X-ray imaging apparatus 100 includes an X-ray generator 110 to generate and radiate X-rays to a subject, an X-ray detector 120 to detect X-rays transmitted through the subject and a controller 130 to analyze an image of the subject and set an X-ray imaging condition or X-ray detection sensitivity according to an analyzed result.

The X-ray generator 110 is connected to a housing 111 to generate and radiate X-rays to the subject. When the subject 30 is a breast, the subject is located between a compression paddle 20 and the X-ray detector 120 and X-rays are radiated to the breast in a state in which the breast is compressed by the compression paddle 20.

The X-ray generator 110 receives power form a power supply (not shown) and generates X-rays. X-ray energy level may be controlled by tube voltage or X-ray flux or X-ray dose, which may be controlled by tube current and X-ray exposure time.

The X-ray generator 110 radiates monochromatic X-rays or polychromatic X-rays. As an exemplary embodiment, the X-ray generator 110 may radiate polychromatic X-rays having a predetermined energy band and the energy band of the radiated X-rays is defined by an upper limit and a lower limit.

The upper limit of the energy band, that is, maximum energy of radiated X-rays, is controlled by a level of the tube voltage and the lower limit of the energy band, that is, minimum energy of radiated X-rays, may be controlled by a filter provided inside or outside the X-ray generator. 110 When X-rays of a low energy band are filtered by the filter, average energy of radiated X-rays may be increased.

The X-ray detector 120 may be implemented in a semiconductor device such as a charge coupled device (CCD), a complementary metal-oxide semiconductor (CMOS) device or a thin film transistor (TFT) and detects X-rays transmitted through the subject and converts the detected X-rays into an electrical signal. A method of converting detected X-rays into an electrical signal may include a direct conversion method and an indirect conversion method. The direct conversion method uses photoconductors to generate charges by absorption of X-rays and the indirect conversion method allows X-rays transmitted through the subject to react with a scintillator to emit photons having a visible light wavelength and converting the photons into charges by a light receiving element. The X-ray imaging apparatus 100 is not limited in terms of the X-rays detection method or implementation of the X-ray detector 120. In this exemplary embodiment, for convenience of description, it is assumed that the X-ray detector 120 is implemented in a CMOS device.

The X-ray detector 120 includes a plurality of light receiving elements such as photodiodes, which are provided in respective pixels. The plurality of light receiving elements converts X-rays transmitted through the subject into charges and an amplification circuit included in the X-ray detector 120 amplifies an electrical signal corresponding to an amount of charges to output the amplified signal. Here, the electrical signal may be a voltage signal.

Here, the amplification circuit may include an amplifier to amplify the electrical signal to an appropriate level and to output the amplified signal. An amplification ratio of the electrical signal is referred to as gain, and gain of the X-ray detector 120 is referred to as detection sensitivity.

X-rays radiated by the X-ray generator 110 are attenuated while transmitting through the subject. Since the attenuation rate of X-rays is changed according to, for example, properties of tissues configuring a part of a human body, i.e., the subject, to which X-rays are radiated or a thickness of the part of the human body to which X-rays are radiated, an amount of detected X-rays varies according to an internal configuration of the subject. Based on the electrical signals converted by the X-ray detector 120 with respect to the plurality of pixels, the subject is imaged. The electrical signal may be an image signal. The image signal is transmitted to the controller 130 and the image signal transmitted to the controller 130 may be an analog signal or a digital signal.

The controller 130 analyzes the image signal received from the X-ray detector 120 and sets gain of each detection region of the X-ray detector 120 according to the properties of the subject. The X-ray detector 120 includes a plurality of pixel regions. A pixel region is a detection unit including a light receiving element and a detection region of the X-ray detector 120 includes at least one pixel region.

The image signal analyzed by the controller 130 may be acquired by pre-shot or main shot. Hereinafter, pre-shot will be described.

An imaging condition of the X-ray imaging apparatus 100 includes tube voltage, tube current, an X-ray exposure time, a filter, an anode (i.e., target material), etc. The controller 130 may set the imaging condition to an appropriate value by using information about the subject obtained through pre-shot and the X-ray imaging apparatus may perform main shot after the imaging condition has been appropriately set.

Pre-shot is performed by radiating X-rays to the subject in a state in which tube current and X-ray exposure time are less than those of normal shot. The controller 130 analyzes the image signal acquired by pre-shot and sets the imaging condition. In an exemplary embodiment, a representative value of intensity of X-rays detected upon performing pre-shot is calculated and an imaging condition of main shot is directly calculated from information about the subject, for example, thickness or compression strength of the subject. A condition of the pre-shot and the representative value of the intensity of X-rays in the pre-shot or an optimal imaging condition set based thereon may be stored in a database to be retrieved later for a corresponding imaging condition.

Hereinafter, a case in which the image signal analyzed by the controller 130 is acquired by main shot will be described. When the pre-shot is not performed, target intensity of X-rays is set using information such as thickness, compression strength, etc. about the subject obtained without analysis of the image signal and main shot is performed to radiate X-rays. The X-ray detector 120 may measure the intensity of X-rays in real time and stop X-ray radiation once the intensity of X-rays reaches the target intensity. In addition to the above method, a method of setting a target exposure time and stopping X-ray radiation when an X-ray exposure time reaches the target exposure time may be used. In addition, a user may directly perform or stop X-ray radiation and a method of acquiring an image signal by a controller without pre-shot is not limited.

Once X-ray radiation is completed, the X-ray detector 120 detects X-rays and transmits an image signal of the subject to the controller 130. The controller 130 analyzes the received image signal and sets gain according to the properties of the detection regions of the subject detected by the X-ray detector 120.

When the gain of the X-ray detector 120 is controlled according to settings of the controller 130, information about X-rays transmitted through the subject, which is temporarily or non-temporarily stored in the X-ray detector 120, is converted into an electrical signal. The converted electrical signal is amplified according to gain of the X-ray detector 120 and is transmitted to the controller 130, thereby generating an X-ray image.

Hereinafter, operation of the controller 130 will be described in detail.

Figure 3:
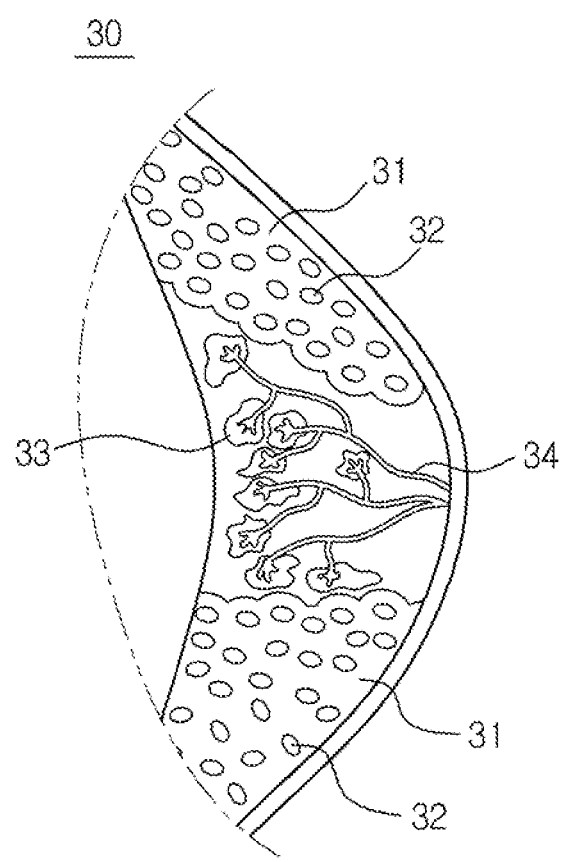
FIG. 3 is a cross-sectional view of a subject which is a breast.
Figure 4:
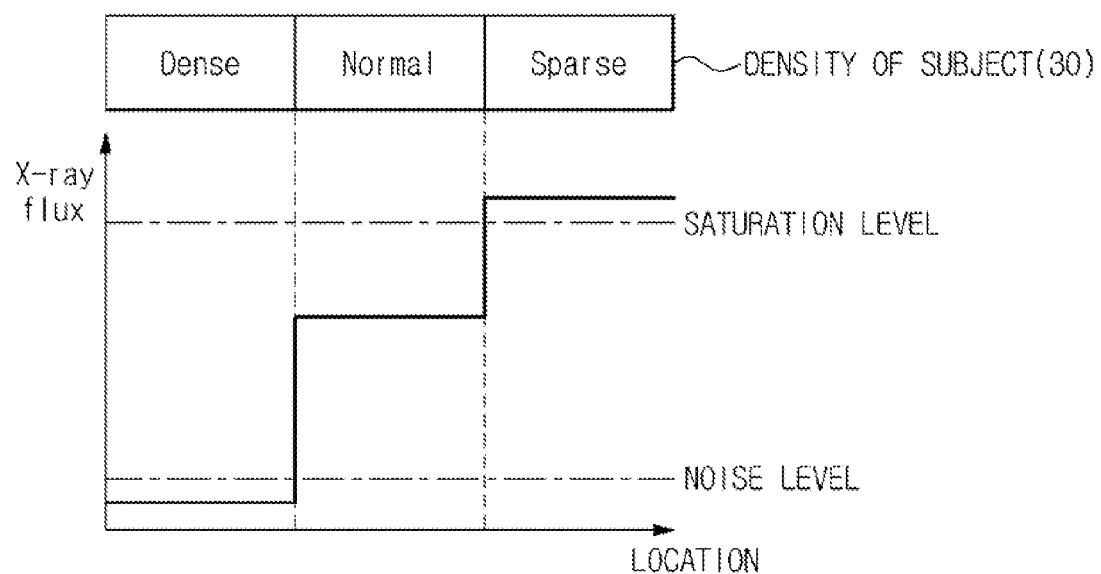
FIG. 4 is a graph schematically showing X-ray flux through a subject.

FIG. 3 is a cross-sectional view of a subject which is a breast, and FIG. 4 is a graph schematically showing X-ray flux through a subject.

Referring to FIG. 3, tissues of a breast 30 include fibrous tissues 31 supporting the breast 30 and maintaining a shape of the breast 30, adipose tissues 32 distributed in the entire breast 30, mammary glands 33 to produce milk and lactiferous ducts 34 which are passages via which milk moves. Among others, tissues used to produce and supply milk, such as the mammary glands 33 and the lactiferous ducts 34, are referred to as parenchyma of the breast 30. In the parenchyma, attenuation of X-rays is increased. Accordingly, an X-ray image of a part having much parenchyma may be brighter, e.g., a white color. Therefore, a part having much parenchyma has higher density.

When the thickness of the subject through which X-rays transmit is larger or the density of the subject is higher, attenuation of X-rays is increased and thus X-ray flux through the subject is decreased. On the other hand, when the thickness of the subject through which X-rays transmit is smaller or the density of the subject is lower, attenuation of X-rays is decreased and thus X-ray flux through the subject is increased.

Even in a subject 30 having substantially uniform thickness, the density thereof may still be varied according to location within the subject 30. For example, when the subject 30 is a breast, as shown in FIGS. 2 and 3, even when the breast 30 is compressed by the compression paddle 20 to have substantially uniform thickness, the breast 30 includes a part in which the density of the parenchyma is higher and a part in which the density of the parenchyma is lower according to tissue distribution of the breast 30.

As shown in FIG. 4, when it is assumed that the subject 30 has a first region (dense) having higher density, a second region (normal) having medium density and a third region (sparse) having lower density. Since variation in thickness or density of the subject 30 according to regions of the subject 30 is not considered when the controller 130 sets the imaging condition or performs main shot without pre-shot, when X-rays are radiated to the subject 30, X-ray flux through the first region (dense) is lowest and X-ray flux through the third region (sparse) is highest.

A level of the electrical signal amplified and output by the X-ray detector 120 is limited. Accordingly, when the density of the third region (sparse) is very lower, as shown in FIG. 4, the electrical signal corresponding to X-rays transmitted through the third region (sparse) may be saturated. On the other hand, when the density of the first region (dense) is very higher, the electrical signal corresponding to X-rays transmitted through the first region (dense) may be mixed with noise, thereby generating an image having lower quality.

Accordingly, the controller 130 analyzes the image signal of the subject and varies the gain of the X-ray detector 120 according to the thickness or density of the region of the subject, that is, according to a level of the image signal of the region of the subject. For example, gain of the X-ray detector 120 may be set to be higher with respect to a region of the subject, the thickness or density of which is larger (a region corresponding to a lower brightness image signal), thereby reducing a noise region, and is set to be lower with respect to a region of the subject, the thickness or density of which is smaller (a region corresponding to a higher brightness image signal), thereby reducing a saturation region.

Figure 5:
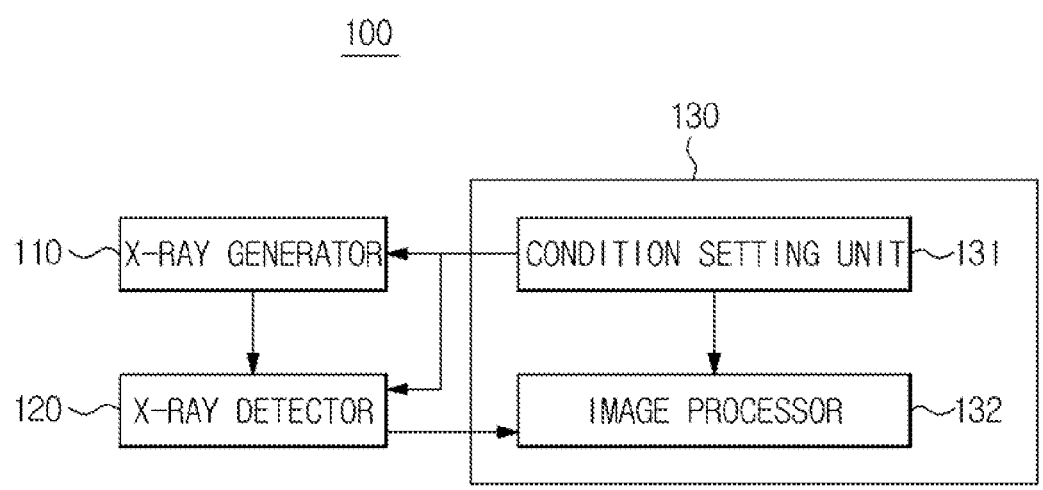
FIG. 5 is a block diagram of an X-ray imaging apparatus according to an exemplary embodiment.

FIG. 5 is a block diagram of an X-ray imaging apparatus according to an exemplary embodiment. Hereinafter, operation of the X-ray imaging apparatus according to an exemplary embodiment will be described in detail with reference to FIG. 5.

In an exemplary embodiment of FIG. 5, basic operations of an X-ray generator 110 and an X-ray detector 120 are substantially the same as those described with respect to FIG. 1 and a description thereof will be omitted.

The controller 130 includes a condition setting unit 131 to analyze the image signal acquired by the X-ray detector 120 and to set the gain of the X-ray detector 120 to correspond to the thickness or density of a region of a subject and an image processor 132 to perform gain correction with respect to the image signal output from the X-ray detector 120 according to the gain set by the condition setting unit 131.

Figure 6A:
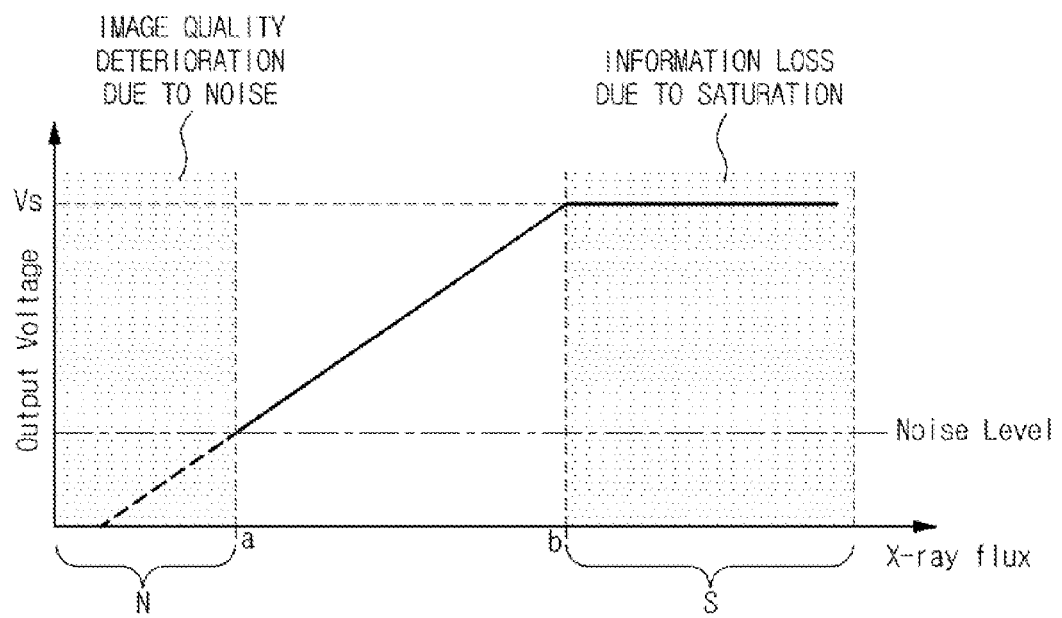
FIG. 6A is a graph schematically showing variation in output voltage of an X-ray detector according to X-ray flux through a subject.
Figure 6B:
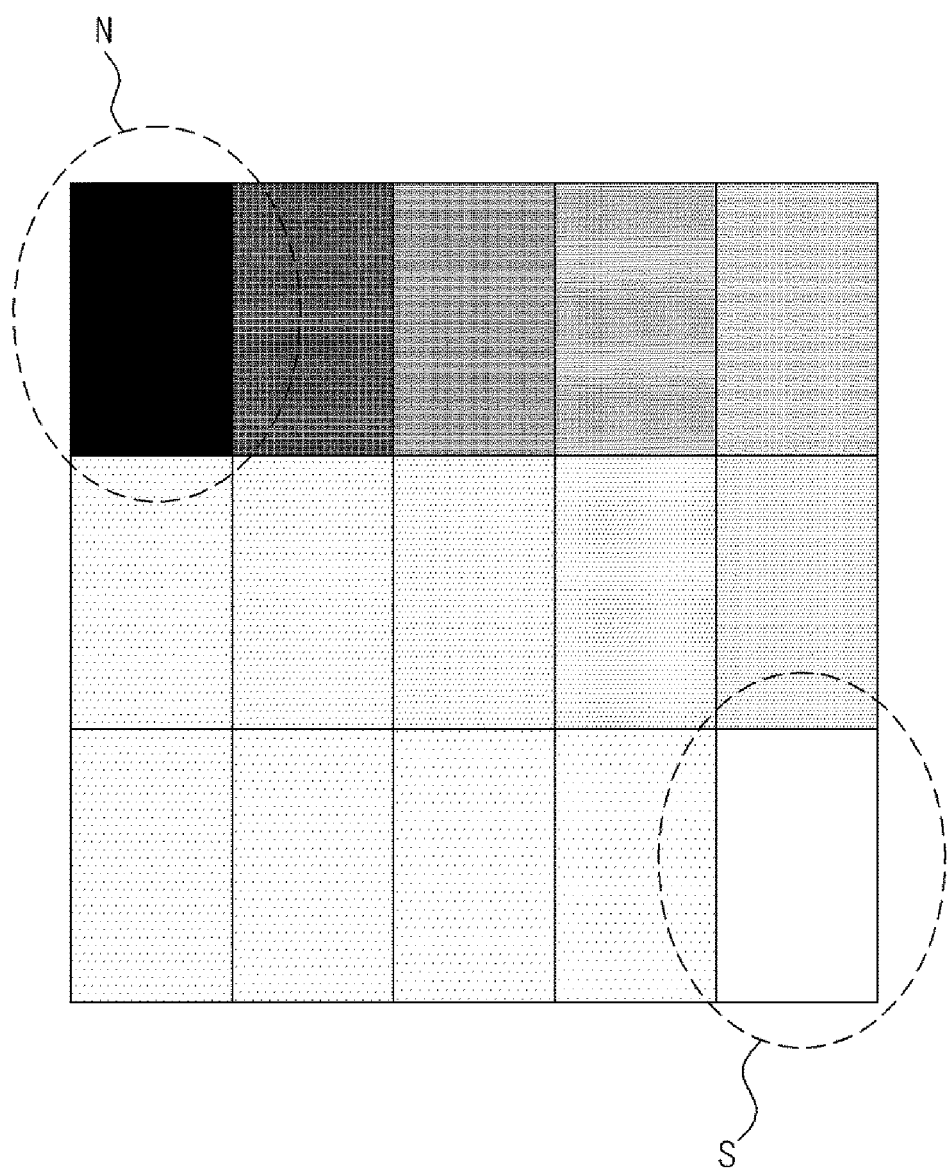
FIG. 6B is a graph schematically showing a raw image including a noise region and a saturation region.

FIG. 6A is a graph schematically showing variation in output voltage of an X-ray detector according to X-ray flux through a subject, and FIG. 6B is a graph schematically showing a raw image including a noise region and a saturation region.

Herein, the intensity of X-rays is represented by X-ray flux, that is, a number of photons per unit time.

The graph of FIG. 6A shows the output value of the X-ray detector 120 in a single pixel region when original gain is applied. That is, in the graph of FIG. 6A, a slope represents the original gain. The original gain may be set as a default value in the X-ray detector 120 or may be set according to the intensity of X-rays set by pre-shot when the pre-shot is performed.

X-rays transmitted through the subject and detected by the X-ray detector 120 are amplified by predetermined gain and is output as an amplified voltage signal. Referring to FIG. 6A, as the intensity of X-rays transmitted through the subject increases, a level of the output voltage signal is increased. However, as described above, since the level of the voltage signal amplified and output by the X-ray detector 120 is limited, when X-ray flux through the subject is equal to or greater than X-ray flux b corresponding to saturation voltage Vs, the voltage signal corresponding thereto is saturated.

Accordingly, when X-ray flux through the subject is equal to or greater than the X-ray flux b, image information of the subject is lost. Hereinafter, the region in which detected X-ray flux is equal or greater than the X-ray flux b, that is, a region in which an output voltage signal is saturated, among detection regions of the X-ray detector 120 is referred to as a saturation region S. Referring to FIG. 6B, a part corresponding to the saturation region S in a raw image may be brighter, e.g., a white color. Thus, it is difficult to confirm information about the subject in the saturation region S.

The voltage signal output from the X-ray detector 120 includes noise and a voltage signal having a level less than a noise level generates an X-ray image having lower quality due to noise. Hereinafter, a region in which X-ray flux is less than X-ray flux a, that is, a region in which the output voltage signal is less than the noise level, among the detection regions of the X-ray detector 120 is referred to as a noise region N. Referring to FIG. 6B, a part corresponding to the noise region N in the raw image has lower quality than that of other parts.

A level difference between a maximum signal and a minimum signal measured by the X-ray detector 120 without noise or saturation is referred to as a dynamic range. In the graph of FIG. 6A, a range between the X-ray flux a and the X-ray flux b is the dynamic range. By increasing the dynamic range, it is possible to acquire a higher contrast X-ray image.

Accordingly, the condition setting unit 131 analyzes an image signal acquired by the X-ray detector 120 by pre-shot or main shot and controls gain of each detection region of the X-ray detector 120, thereby extending the dynamic range of the X-ray image.

The condition setting unit 131 analyzes the image signal acquired by pre-shot and extracts the noise region and the saturation region. Gain of the X-ray detector 120 is set to be higher with respect to the noise region and gain of the X-ray detector 120 is set to be lower with respect to the saturation region.

In an exemplary embodiment of extracting the noise region and the saturation region, the condition setting unit 131 estimates X-ray dose to be radiated upon performing the main shot and determines whether each of a plurality of detection regions of the X-ray detector 120 corresponds to the noise region or the saturation region based on the estimated dose.

Each of the plurality of detection regions includes at least one pixel region. When each detection region includes a pixel region, an image signal output in each pixel region is used and, when each detection region includes a plurality of pixel regions, an average value of image signals output from the plurality of pixel regions may be used. In this exemplary embodiment, for convenience of description, each detection region includes a pixel region.

For example, when output voltage of any pixel region in an image signal acquired by pre-shot is 2V and the X-ray dose to be radiated upon performing the main shot is set to twice that of the pre-shot, the output voltage of this pixel region may be estimated to 4V upon performing the main shot. In addition, even when a relationship between the X-ray dose to be radiated and the output signal is not linear, the relationship between the X-ray dose to be radiated and the output signal may be predicted.

The predicted output voltage and the saturation voltage of the X-ray detector 120 are compared. When the predicted output voltage is equal to or greater than the saturation voltage, it is determined that the pixel region corresponds to the saturation region. When the predicted output voltage is less than the saturation voltage, the predicted output voltage is compared with the noise level. When the predicted output voltage is less than or equal to the noise level, the pixel region is determined to correspond to the noise region.

Namely, the condition setting unit 131 compares the level of the image signal output in the pixel region of the X-ray detector 120 with a first reference level corresponding to the saturation voltage or a second reference level corresponding to the noise level. The image signal is in the saturation region when the image signal is equal to or greater than the first reference level and is in the noise region when the image signal is equal to or less than the second reference level.

The first reference level and the second reference level are signal levels based on a relationship between the X-ray dose to be radiated in the pre-shot and the X-ray dose to be radiated in the main shot. However, when X-rays are radiated in the main shot without performing the pre-shot, the first reference level becomes a saturation voltage level and the second reference level becomes a noise level in the main shot.

The condition setting unit 131 may perform the above-described determination with respect to all pixel regions of the X-ray detector 120 or a pixel region in which the subject is imaged.

The condition setting unit 131 sets gain of the X-ray detector 120 to be lower with respect to a pixel region corresponding to the saturation region and sets gain of the X-ray detector 120 to be higher with respect to a pixel region corresponding to the noise region.

Figure 7:
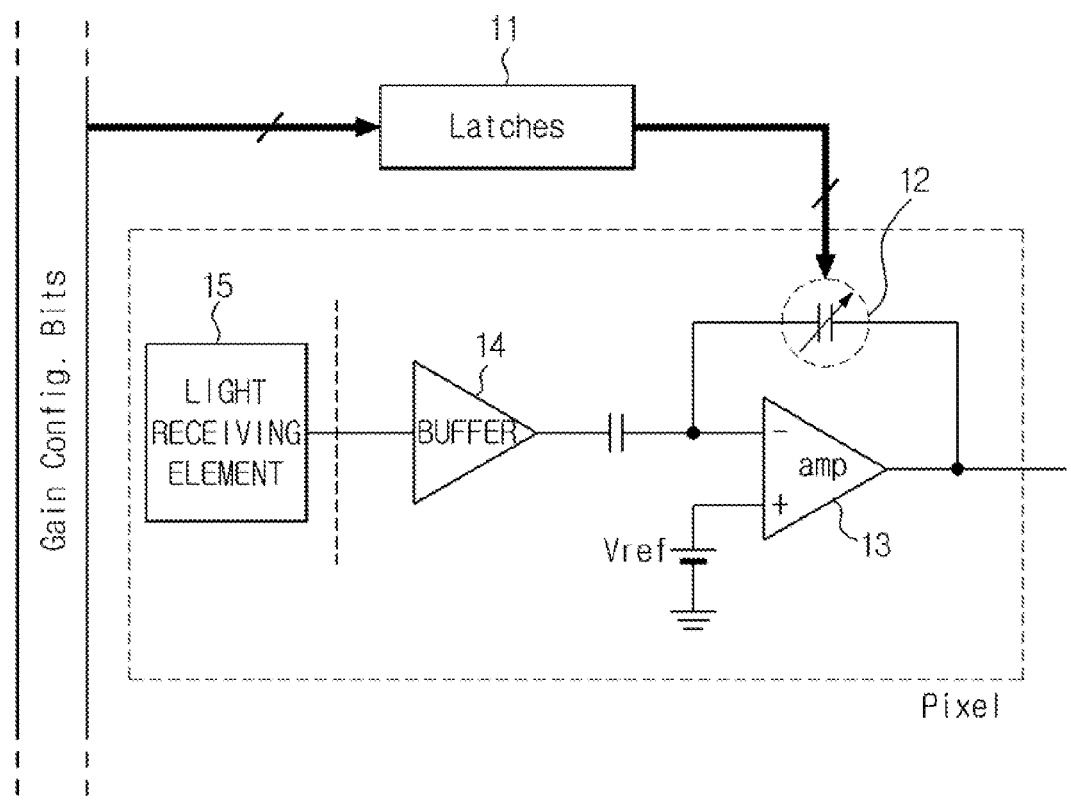
FIG. 7 is a schematic circuit diagram showing a structure of a pixel region in an X-ray imaging apparatus according to an exemplary embodiment.

FIG. 7 is a schematic circuit diagram showing a structure of a pixel region in an X-ray imaging apparatus according to an exemplary embodiment.

Referring to FIG. 7, a pixel region may include a light receiving element 15 to detect and convert X-rays into charges and an amplification circuit to read the amount of charges and output a voltage signal. The light receiving element 15 may be implemented by a PN photodiode, a PIN photodiode, a Schottky photodiode, an avalanche photodiode, etc.

When charges flow in the light receiving element 15, the flow of charges forms current and this current is input to an amplifier 13 through a buffer 14 of the amplification circuit to output an amplified voltage signal. Gain of the amplifier 13 is controlled by a variable capacitor 12 and the condition setting unit 131 controls capacity of the variable capacitor 12 through a latch 11. Gain of the pixel region corresponding to the saturation region or the noise region is dynamically controlled to the set value and the amplification circuit becomes a gain control circuit. The gain control circuit may independently control gain of each of the plurality of light receiving elements 15 according to a value set by the condition setting unit 131.

FIG. 7 shows the pixel region when the X-ray detector 120 is of a CMOS type. When the X-ray detector 120 is of a TFT type, the gain control circuit is not included in each pixel region and gain is controlled on a column basis when data is read out in a row direction.

A region which does not correspond to the saturation region or the noise region among the detection regions of the X-ray detector 120 may maintain original gain. A criterion for setting gain by the condition setting unit 131 may be determined based on the original gain, gain lower than the original gain set with respect to a pixel region corresponding to the saturation region, and gain higher than the original gain set with respect to a pixel region corresponding to the noise region. The value of the set gain may be determined in consideration of the level of a signal to be output in the pixel region, the saturation level, and the noise level. A value having an appropriate (e.g., optimal) intensity level under given conditions may be mapped through experimentation or simulation.

Figure 8A:
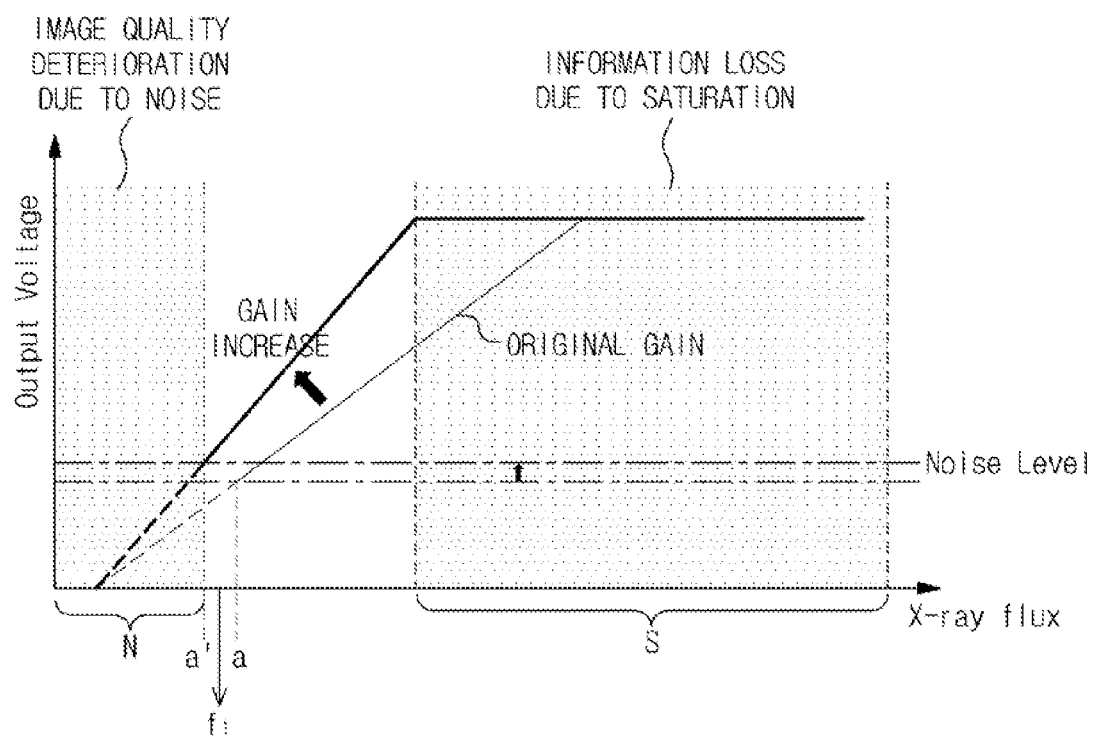
FIG. 8A is a graph showing a relationship between output voltage and X-ray flux in a saturation region or a noise region when gain of a pixel region increases.
Figure 8B:
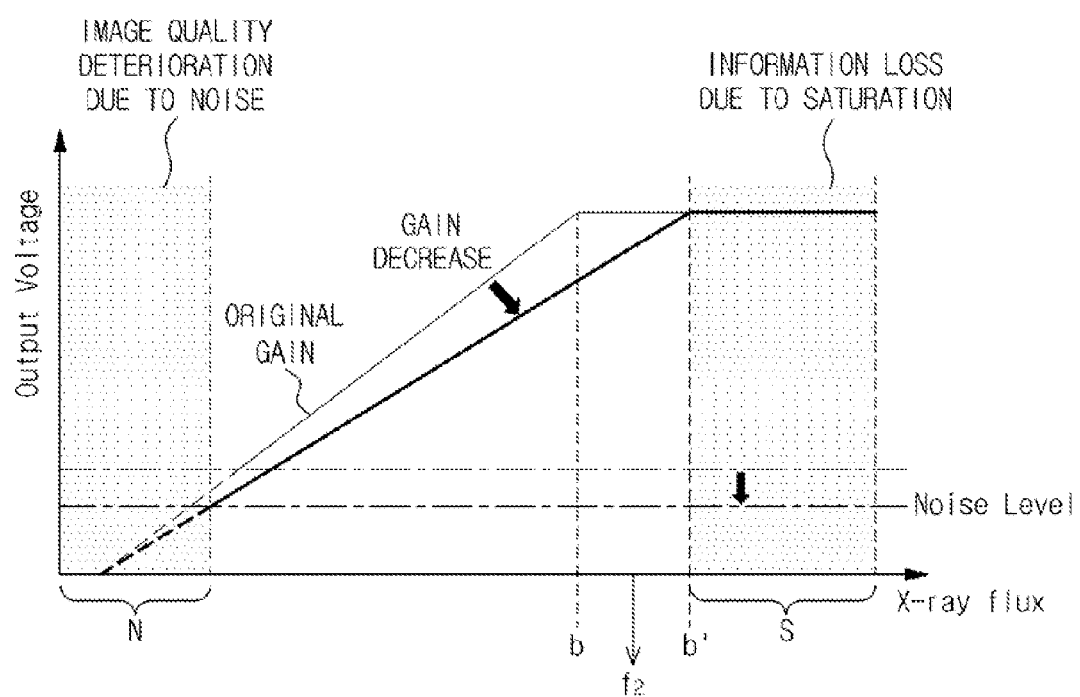
FIG. 8B is a graph showing a relationship between output voltage and X-ray flux in a saturation region or a noise region when gain of a pixel region decreases.

FIG. 8A is a graph showing a relationship between output voltage and X-ray flux in a saturation region or a noise region when gain of a pixel region increases, and FIG. 8B is a graph showing a relationship between output voltage and X-ray flux in a saturation region or a noise region when gain of a pixel region decreases. The graphs of FIGS. 8A and 8B may correspond to a single pixel region.

As shown in FIG. 8A, when gain of the pixel region is increased, that is, when gain higher than the original gain is set, a voltage signal greater than a voltage signal output in case of setting the original gain is output with respect to the same amount of X-rays input to the pixel region.

When gain is increased, noise included in a signal is amplified and noise level is increased accordingly. However, as shown in FIG. 8A, when the slope of the graph, i.e., gain is increased, X-ray flux at which a voltage signal reaches the noise level is decreased (a→a').

More specifically, when the number of photons (i.e., X-ray flux) input to the pixel region per unit time through the subject is $f_1$, the pixel region corresponds to the noise region when the original gain is applied. On the other hand, the X-ray flux $f_1$ does not correspond to the noise region when gain set by the condition setting unit 131 is applied according to a graph represented in a bold line in FIG. 8A. That is, image quality may not be deteriorated due to noise at the X-ray flux $f_1$. Thus, overall image quality may be improved.

As shown in FIG. 8B, when gain of the pixel region is reduced, that is, when gain is controlled to be lower than the original gain, a voltage signal less than a voltage signal output in case of setting the original gain is output with respect to the same amount of X-rays input to the pixel region.

Accordingly, X-ray flux at which the output signal starts to be saturated increases (b→b'). When the number of photons (i.e., X-ray flux) input to the pixel region per unit time through the subject is $f_2$, the pixel region corresponds to the saturation region when the original gain is applied. On the other hand, the X-ray flux $f_2$ does not correspond to the saturation region when gain set by the condition setting unit 131 is applied according to a graph represented in a bold line in FIG. 8B. That is, information loss due to saturation may be avoided at the X-ray flux $f_2$.

The image processor 132 performs image processing with respect to the image signal acquired by the X-ray detector 120 and generates an X-ray image to be displayed on a display (not shown) included in the X-ray imaging apparatus 100. The image signal subjected to image processing by the image processor 100 is an image signal to which gain set by the condition setting unit 131 is applied.

More specifically, when the pre-shot is performed, the image signal acquired by the pre-shot is analyzed to control gain of the X-ray detector 120 and, when X-rays are radiated for the main shot, the X-ray detector 120, gain of which is controlled, detects X-rays and acquires an image signal. This image signal is subjected to image processing by the image processor 132.

Alternatively, when the pre-shot is not performed, the condition setting unit 131 analyzes the image signal acquired from the X-rays radiated for the main shot to control gain of the X-ray detector 120 and charges temporarily stored in the X-ray detector 120 pass through the amplification circuit with controlled gain to output an image signal. This image signal is subjected to image processing by the image processor 132.

The image processing performed by the image processor 132 includes preprocessing and post-processing. In an exemplary embodiment, preprocessing means a process of correcting an entire image of the subject to an image with substantially uniform X-ray detection sensitivity and post-processing means an image improvement or enhancement process.

Flat field correction may be performed per pixel value, that is, a brightness value corresponding to each pixel region. The brightness value is proportional to the intensity of X-rays detected in a corresponding pixel region and may be calculated from an image signal, that is, a voltage signal, output from the corresponding pixel region. The flat field correction may be performed according to Equation 1 below.

$$i_{correct} = -\log\{(i_{measure} - i_{dark})/(i_{white} - i_{dark})\} \quad \text{[Equation 1]}$$

wherein $i_{measure}$ is a pixel value acquired in the main shot, $i_{dark}$ is a pixel value acquired in a state in which X-rays are not radiated, and $i_{white}$ is a pixel value acquired by radiating X-rays on a background without the subject. The $i_{dark}$ and the $i_{white}$ are acquired under substantially the same thickness condition of the subject and substantially the same gain condition of the X-ray detector 120. For example, when the $i_{measure}$ is a pixel value obtained when gain is $G_1$, the $i_{dark}$ and the $i_{white}$ are acquired when gain is $G_1$.

The $i_{dark}$ and the $i_{white}$ may be acquired and stored according to gain and thickness in advance to calculate the flat field correction according to Equation 1. Alternatively, the $i_{dark}$ and the $i_{white}$ acquired under certain gain and thickness conditions may be stored in advance and, based thereon, information about the $i_{dark}$ and the $i_{white}$ under corresponding gain and thickness conditions may be acquired.

Figure 9:
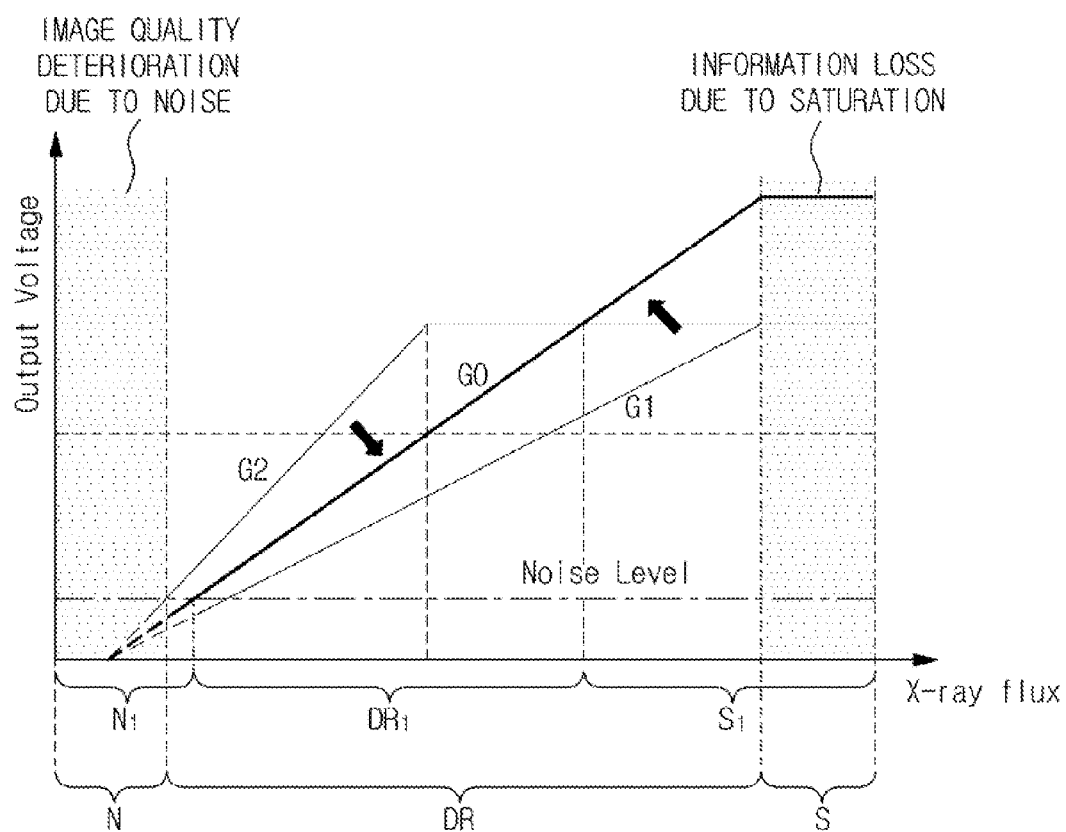
FIG. 9 is a graph showing a dynamic range of an X-ray image when preprocessing is performed in an image processor.

FIG. 9 is a graph showing a dynamic range of an X-ray image when preprocessing is performed in an image processor.

Referring to FIG. 9, when gain of a pixel region corresponding to a saturation region $S_1$ is set to $G_1$ and gain of a pixel region corresponding to a noise region $N_1$ is set to $G_2$, in a case where the flat field correction according to Equation 1 is performed with respect to an output signal of the pixel region corresponding to the saturation region $S_1$ and an output signal of the pixel region corresponding to the noise region $N_1$ according to gain of each pixel region, an image with substantially uniform X-ray detection sensitivity may be obtained and a dynamic range of the obtained image may extend compared to a case in which gain of the entire pixel region is set to $G_0$ ($DR_1 \rightarrow DR$).

When the flat field correction of each pixel region is completed, the image processor 132 performs post-processing for image improvement and enhancement. For example, frequency response properties and intensity of the image may be controlled through intensity processing and frequency processing, quality of a diagnostic image may be improved through spatial frequency processing, and objective image enhancement may be realized through the intensity processing. The image processor 132 may perform post-processing based on gain set per pixel region.

Although offset of the X-ray detector 120 is not considered in the above-described embodiment, the offset may be included in the signal output from the X-ray detector 120. Therefore, the X-ray imaging apparatus 100 according to an exemplary embodiment may perform gain control of the X-ray detector 120 and offset control.

Figure 10:
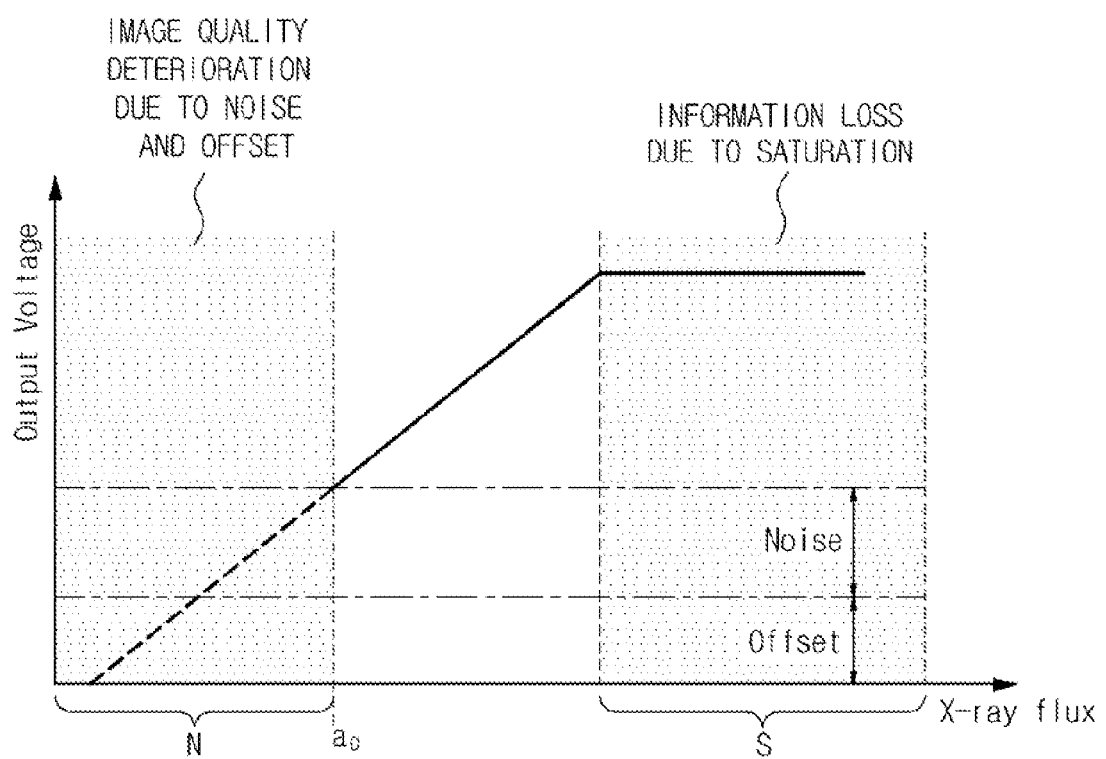
FIG. 10 is a graph showing a relationship among X-ray flux through a subject, output voltage, and offset.

FIG. 10 is a graph showing a relationship among X-ray flux through a subject, output voltage, and offset.

Referring to FIG. 10, offset may be included in the signal output from the X-ray detector 120. When X-rays having flux of $a_0$ or less are detected, image quality may be deteriorated due to noise and offset. That is, the noise region N is extended due to the offset.

Accordingly, the condition setting unit 131 of the X-ray imaging apparatus 100 according to an exemplary embodiment may control gain of each pixel region and also decrease the offset to reduce an image quality deterioration region.

Figure 11:
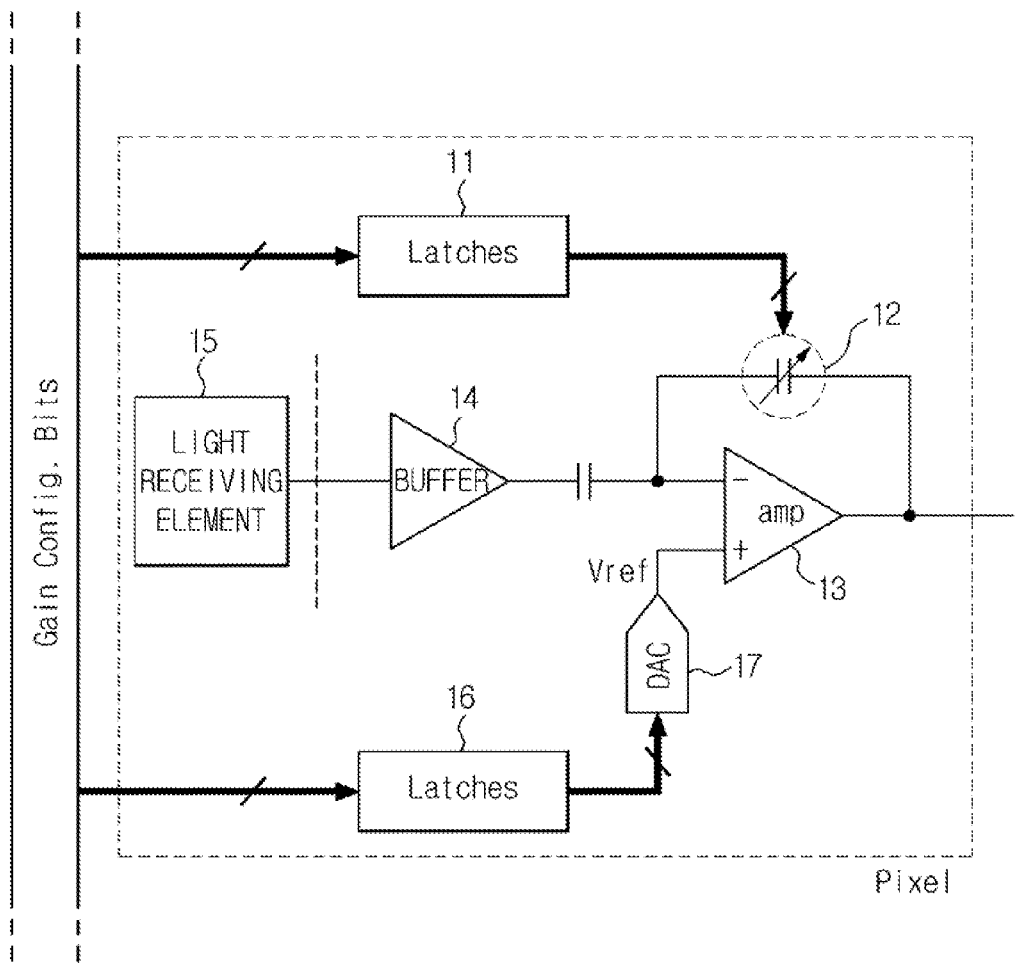
FIG. 11 is a schematic circuit diagram showing a structure of a pixel region, in which offset may be controlled, in an X-ray imaging apparatus according to an exemplary embodiment.

FIG. 11 is a schematic circuit diagram showing a structure of a pixel region, in which offset may be controlled, in an X-ray imaging apparatus according to an exemplary embodiment.

Referring to FIG. 11, a signal corresponding to detected X-ray flux is input to an inverting input terminal (−) of an amplifier 13 and a reference voltage $V_{ref}$ for determining offset is input to a non-inverting input terminal (+) thereof. Here, the input reference voltage may not be set to a ground voltage or a constant voltage but may be externally controlled by a digital latch 16 and a digital-to-analog converter (DAC) 17 connected thereto. Accordingly, the controller 130 may control the reference voltage through the digital latch 16 and the digital-to-analog converter 17 may convert a digital value output from the digital latch 16 into an analog value. Alternatively, the user may control the reference voltage using an input unit (not shown) included in the X-ray imaging apparatus 100.

Figure 12:
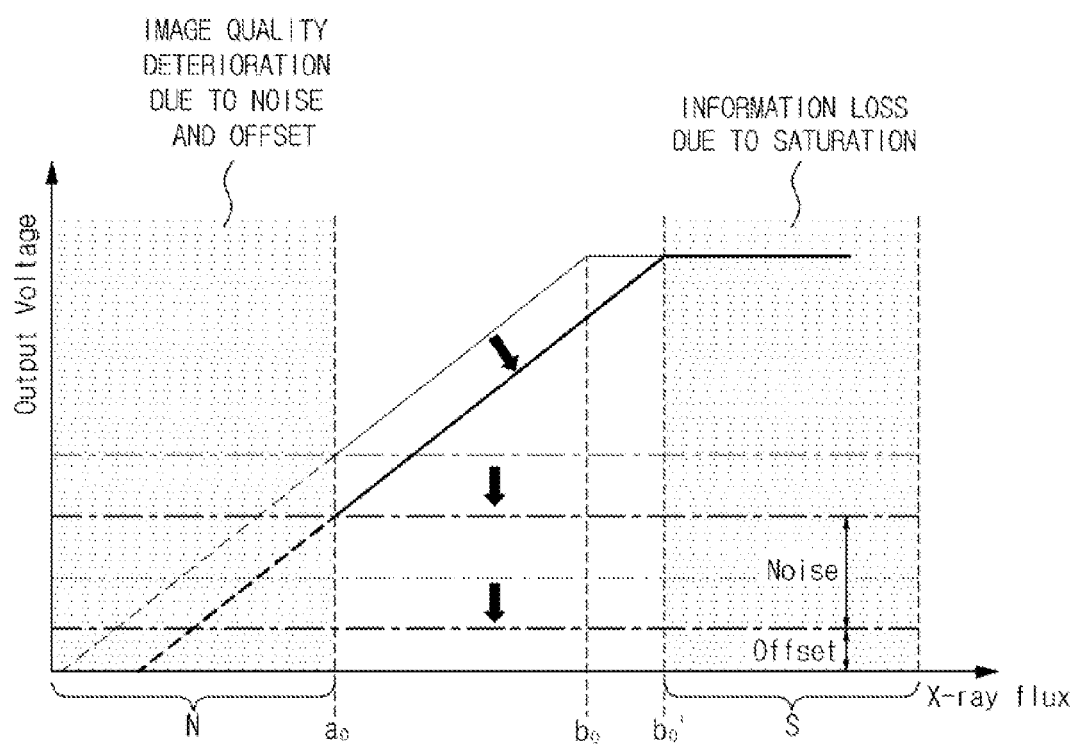
FIG. 12 is a graph showing relationship between output voltage and X-ray flux in a saturation region or a noise region when offset decreases.

FIG. 12 is a graph showing relationship between output voltage and X-ray flux in a saturation region or a noise region when offset decreases. This graph shows a single pixel region.

Referring to FIG. 12, when the offset of a pixel region is controlled to be lower, the graph showing a relationship between X-ray flux and output voltage is shifted to the right. Accordingly, since X-ray flux at which saturation starts is increased ($b_0 \rightarrow b_0'$), information loss due to saturation may be reduced. The condition setting unit 131 may control the offset per pixel region according to the properties of the subject. For example, the offset control may be performed each time the pre-shot or the main shot is performed. In general, a lower offset is advantageous in that the dynamic range of the X-ray image is extended. In particular, when the offset is decreased, X-ray flux at which saturation voltage is reached is increased. Thus, when the offset is set to be lower with respect to the saturation region, information loss due to saturation may be substantially prevented.

Hereinafter, a method of controlling an X-ray imaging apparatus according to an exemplary embodiment will be described.

Figure 13:
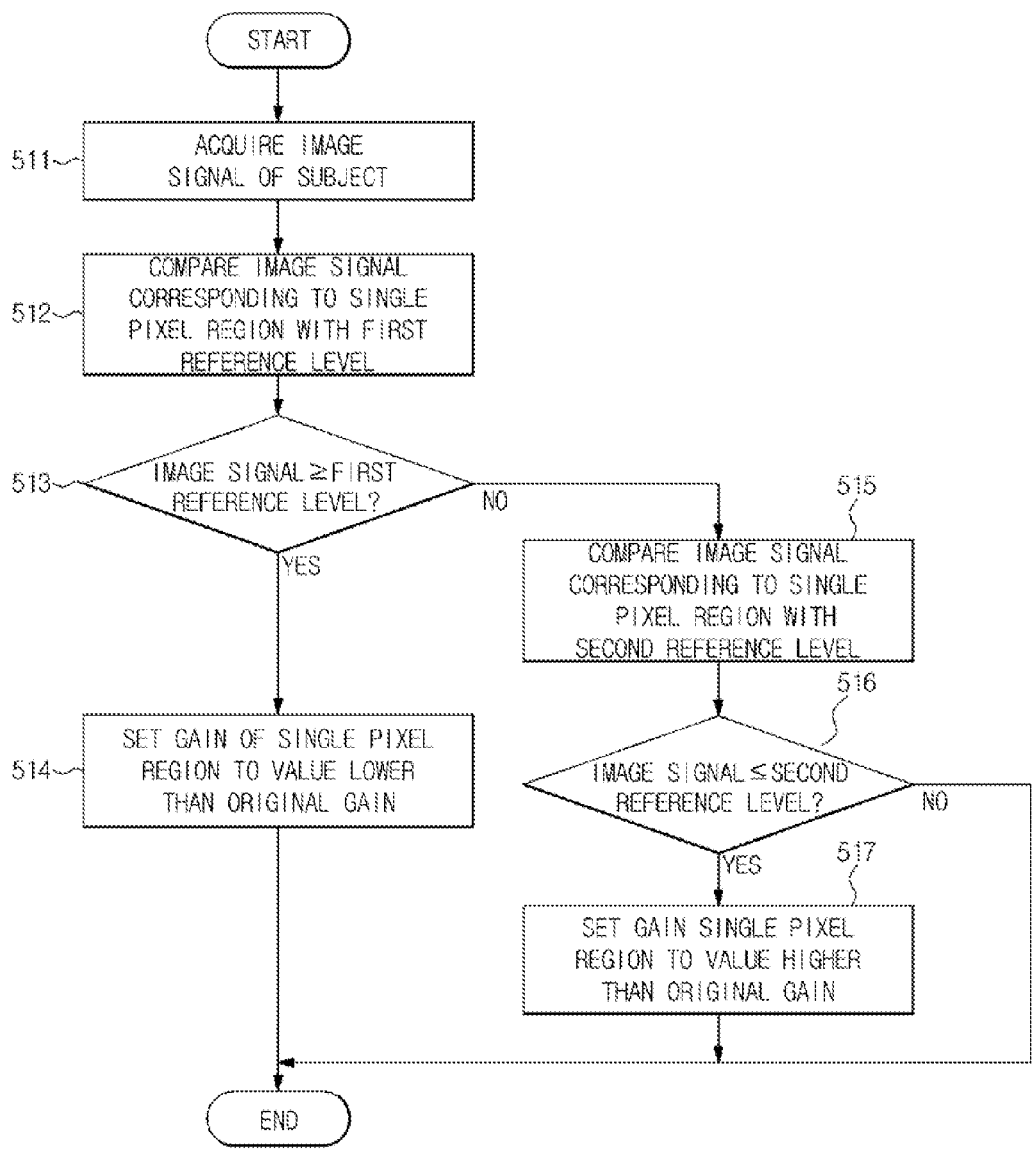
FIG. 13 is a flowchart illustrating a method of setting gain in a method of controlling an X-ray imaging apparatus according to an exemplary embodiment.

FIG. 13 is a flowchart illustrating a method of setting gain in a method of controlling an X-ray imaging apparatus according to an exemplary embodiment.

Referring to FIG. 13, an image signal of a subject is acquired (511). As described in the above exemplary embodiments of the X-ray imaging apparatus, gain of each detection region may be set in the pre-shot or the main shot. Accordingly, the image signal of the subject may be acquired in the pre-shot or the main shot.

The acquired image signal is analyzed and a level of an image signal corresponding to a pixel region is compared with a first reference level (512). Here, the image signal may be a voltage signal output in the pixel region. The first reference level is used to determine whether the pixel region corresponds to a saturation region. When the analyzed image signal is acquired in the pre-shot, the first reference level may be set using a relationship among saturation voltage, X-ray flux in the pre-shot, and X-ray flux in the main shot. When the analyzed image signal is acquired in the main shot, saturation voltage may be used as the first reference level.

When the level of the image signal corresponding to the single pixel region is equal to or greater than the first reference level ('Yes' to 513), it is determined the pixel region is the saturation region and gain of the pixel region is set to a value lower than original gain (514). Here, the set value may be selected from among values pre-mapped through experimentation or simulation. The original gain may be a default value set in the X-ray detector 120.

When the level of the image signal corresponding to the single pixel region is not equal to or greater than the first reference level ('No' to 513), the level of the image signal is compared with a second reference level (515). The second reference level is used to determine whether the pixel region corresponds to a noise region. When the image signal is acquired by the pre-shot, the second reference level may be set using a relationship among a noise level in the pre-shot, X-ray flux in the pre-shot, and X-ray flux in the main shot. When the image signal is acquired by the main shot, the noise level in the main shot may be set as the second reference level.

When the level of the image signal is less than the second reference level ('Yes' to 516), it is determined that the pixel region corresponds to the noise region and gain of the pixel region is set to a value higher than the original gain (517). Here, the set value may be selected from among values pre-mapped through experimentation or simulation.

Operations 511 to 517 may be performed with respect to all pixel regions of the X-ray detectors 120 or regions of interest (i.e., regions in which the subject is to be imaged). Thus, gain may be set according to thickness or density characteristics of each region of the subject.

Figure 14:
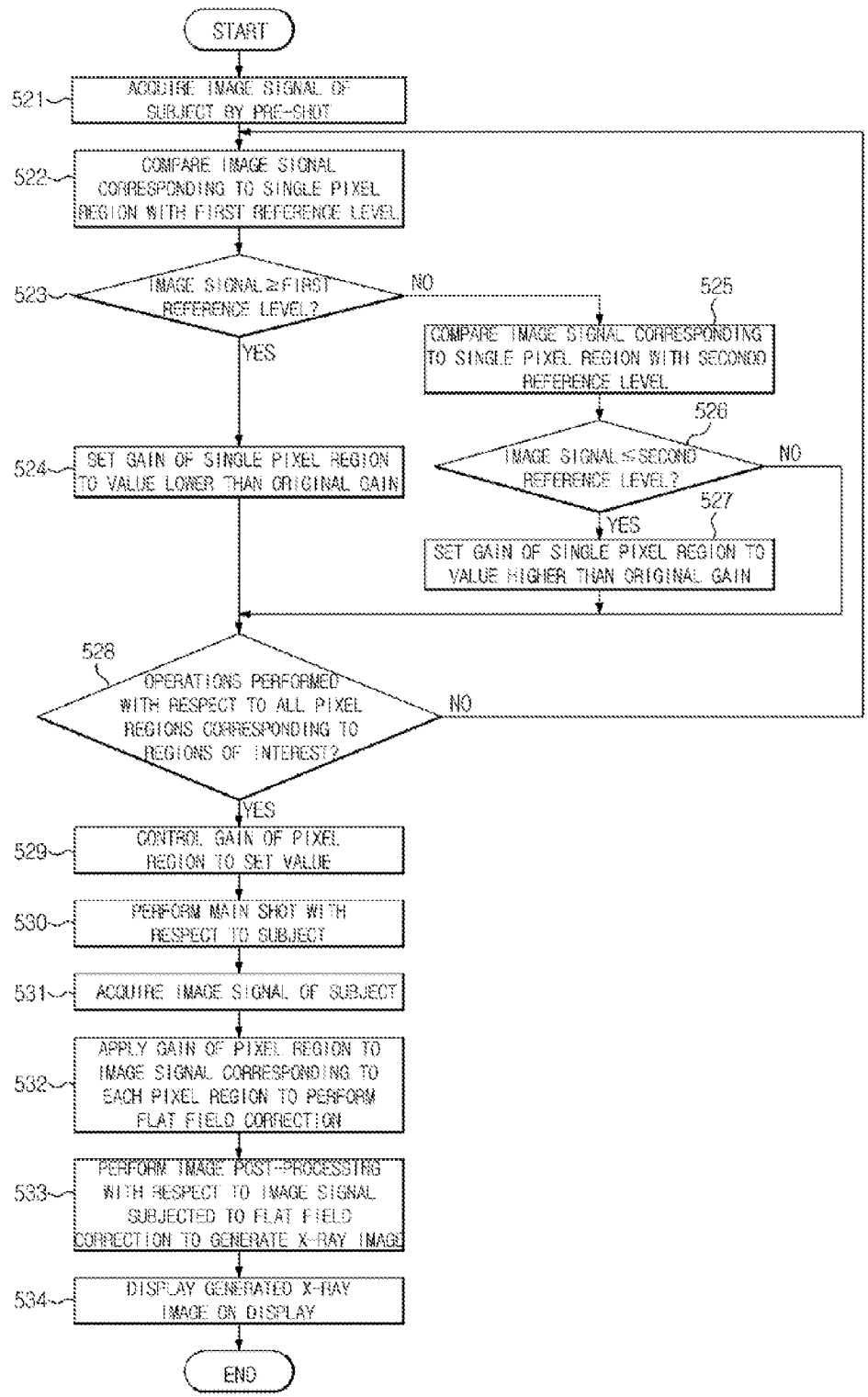
FIG. 14 is a flowchart illustrating a method of setting gain and performing main shot according to the set gain in a method of controlling an X-ray imaging apparatus according to an exemplary embodiment.

FIG. 14 is a flowchart illustrating a method of setting gain and performing main shot according to the set gain in a method of controlling an X-ray imaging apparatus according to an exemplary embodiment.

Referring to FIG. 14, an image signal of a subject is acquired by pre-shot (521). Here, the image signal means an electrical signal output from a plurality of pixel regions corresponding to the subject and may be a converted digital signal.

The level of the image signal corresponding to a single pixel region is compared with a first reference level (522). The first reference level is used to determine whether the pixel region corresponds to a saturation region and is determined in consideration of saturation voltage, X-ray flux in the pre-shot, and X-ray flux in the main shot.

When the level of the image signal is equal to or greater than the first reference level ('Yes' to 523), gain of the single pixel region is set to a value lower than original gain (524). As described above, the set gain value may be selected from among values pre-mapped through experimentation or simulation. The original gain may be a default value set in the X-ray detector 120.

When the level of the image signal is less than the first reference level ('No' to 523), the level of the image signal is compared with a second reference level (525). The second reference level is used to determine whether the pixel region corresponds to a noise region. The second reference level may be set in consideration of a noise level, X-ray flux in the pre-shot, and X-ray flux in the main shot.

When the level of the image signal is less than the second reference level ('Yes' to 526), gain of the pixel region is set to a value higher than the original gain (527). Here, the set gain value may be selected from among values pre-mapped through experimentation or simulation.

When operations 522 to 527 are performed with respect to all pixel regions corresponding to a region of interest ('Yes' to 528), gain of each pixel region may be controlled to each set value (529). Next, main shot is performed with respect to the subject (530). The image signal acquired by the pre-shot is analyzed and imaging conditions such as tube voltage, tube current, X-ray exposure time, etc. to be applied in the main shot are set. The main shot may be performed according to the set imaging conditions.

An image signal of the subject is acquired by main shot (531). Flat field correction is performed with respect to the image signal corresponding to each pixel region according to gain of the pixel region (532). Flat field correction may be performed according to Equation 1 described above.

Image post-processing is performed with respect to the image signal subjected to flat field correction to generate an X-ray image (533) and the generated X-ray image is displayed on the display (534). Image post-processing means an image improvement or enhancement process performed to generate an X-ray image.

Figure 15:
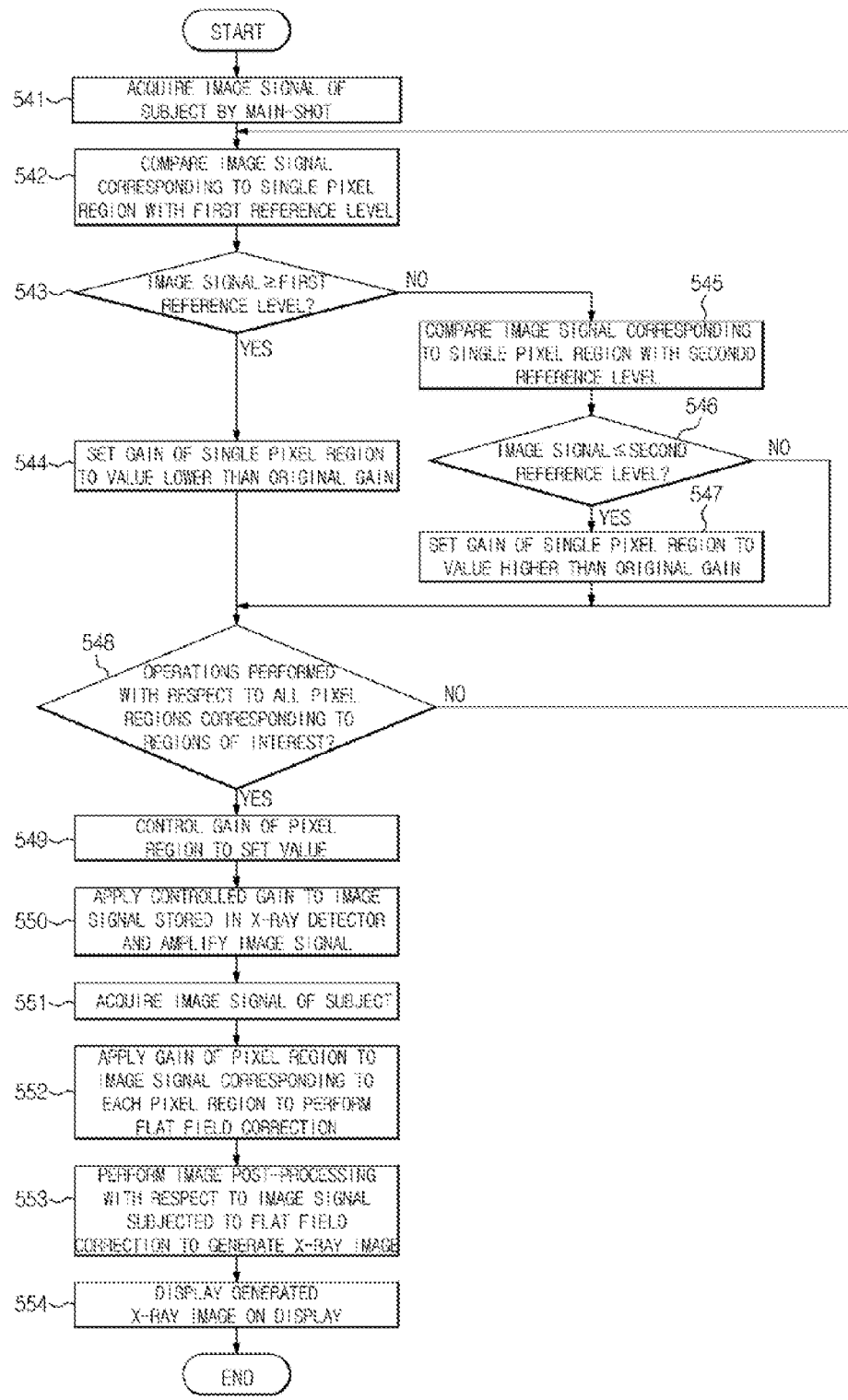
FIG. 15 is a flowchart illustrating a method of setting gain in main shot in a method of controlling an X-ray imaging apparatus according to an exemplary embodiment.

FIG. 15 is a flowchart illustrating a method of setting gain in main shot in a method of controlling an X-ray imaging apparatus according to an exemplary embodiment.

Referring to FIG. 15, X-rays are radiated to acquire an image signal of a subject (541). Here, X-rays are radiated in main shot and a dose of radiated X-rays may be set according to a type, thickness, etc. of the subject.

A level of the image signal corresponding to a single pixel region is compared with a first reference level (542). The first reference level is used to determine whether the pixel region corresponds to a saturation region and saturation voltage level may be set as the first reference level.

When the level of the image signal is equal to or greater than the first reference level ('Yes' to 543), gain of the single pixel region is set to a value lower than original gain (544). Here, the set value may be selected from among values pre-mapped through experimentation or simulation. The original gain may be a default value set in the X-ray detector 120.

When the level of the image signal is less than the first reference level, it is determined that the pixel region does not correspond to the saturation region and the level of the image signal is compared with a second reference level (545). When the level of the image signal is less than the second reference level ('Yes' to 546), gain of the single pixel region is set to a value higher than the original gain (547). Here, the set gain value may be selected from among values pre-mapped through experimentation or simulation.

When operations 541 to 547 have been performed with respect to regions of interest ('Yes' to 548), gain of each pixel region is controlled to each set value (549).

Charges temporarily or non-temporarily stored in the X-ray detector 120 are amplified according to the controlled gain (550).

The image signal of the subject is acquired from the amplified signal (551) and image processing is performed with respect to the acquired image. Image processing may be divided into preprocessing and post-processing.

Preprocessing means a process of correcting the entire image of the subject to an image with substantially uniform X-ray detection sensitivity. For preprocessing, gain of each pixel region is applied to the image signal corresponding to each pixel region to perform flat field correction (522).

Image post-processing is performed with respect to the image signal subjected to flat field correction to generate an X-ray image (553). Image post-processing is applied to a general X-ray image for image improvement or image enhancement.

The generated image is displayed on the display (554).

Although not shown in the flowcharts of FIGS. 13 to 15, in operation to control gain of the X-ray detector 120, an operation to control reference voltage to reduce offset may also be performed. The operation to reduce offset may be performed with respect to all pixel regions, regions of interest, or a saturation region.

According to an X-ray imaging apparatus and a method of controlling the same according to exemplary embodiments, gain of each detection region of an X-ray detector is set according to thickness or density characteristics of a subject. Thus, dynamic range of an X-ray image may be extended to obtain a higher contrast X-ray image.

According to an X-ray imaging apparatus and an X-ray imaging method of exemplary embodiments, it is possible to control sensitivity or gain of X-ray detection based on thickness, density, or X-ray attenuation properties of a subject. Therefore, images with a higher dynamic range may be provided corresponding to various thicknesses, densities or X-ray attenuation properties of the subject.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An X-ray imaging apparatus comprising:
    an X-ray generator configured to generate and radiate X-rays to a subject;
    an X-ray detector including a plurality of detection regions, wherein each of the detection regions includes at least one pixel region and configured to detect and convert X-rays transmitted through the subject into an image signal; and
    a controller configured to analyze the image signal of the subject to extract a noise region and a saturation region from the image signal and set gain of the X-ray detector for each of detection regions of the X-ray detector according to the extracted noise region and the saturation region.

2. The X-ray imaging apparatus according to claim 1, wherein the controller determines a detection region, a level of an image signal of which is equal to or greater than a first reference level, among the detection regions of the X-ray detector as the saturation region and determines a detection region, a level of an image signal of which is equal to or less than a second reference level, among the detection regions of the X-ray detector as the noise region.

3. The X-ray imaging apparatus according to claim 2, wherein the controller sets a value higher than original gain as gain with respect to the noise region of the X-ray detector and sets a value lower than the original gain as gain with respect to the saturation region of the X-ray detector, wherein the original gain is gain of the X-ray detector applied when the analyzed image signal is obtained.

4. The X-ray imaging apparatus according to claim 1, wherein the controller sets offset according to the detection regions of the X-ray detector,
    wherein the X-ray detector includes a gain control circuit configured to receive the gain set by the controller and control the gain of the X-ray detector and an offset control circuit configured to receive offset set by the controller and control offset of the X-ray detector.

5. The X-ray imaging apparatus according to claim 2, wherein the X-ray generator radiates the X-rays to the subject for pre-shot, and the image signal analyzed by the controller is an image signal converted from the X-rays radiated to the subject in the pre-shot.

6. The X-ray imaging apparatus according to claim 5, wherein:
    the first reference level is set using a saturation voltage level of the X-ray detector, X-ray flux in the pre-shot and X-ray flux in main shot, and
    the second reference level is set using a noise level of the X-ray detector in the pre-shot, X-ray dose radiated in the pre-shot and X-ray dose radiated in the main shot.

7. The X-ray imaging apparatus according to claim 6, wherein the X-ray detector controls the gain of the detection region according to the gain set by the controller, converts X-rays transmitted through the subject in the main shot into an image signal, and amplifies and outputs the image signal according to the controlled gain.

8. The X-ray imaging apparatus according to claim 2, wherein the X-ray detector controls the gain of the detection region according to the gain set by the controller and amplifies and outputs the image signal stored in the X-ray detector again according to the controlled gain.

9. The X-ray imaging apparatus according to claim 8, wherein the first reference level corresponds to a saturation voltage level of the X-ray detector and the second reference level corresponds to a noise level of the X-ray detector.

10. The X-ray imaging apparatus according to claim 7, wherein the controller performs correction to compensate for a difference in gain between detection regions with respect to the image signal amplified and output according to the set gain.

11. The X-ray imaging apparatus according to claim 10, wherein the controller performs flat field correction with respect to an output signal of a pixel region corresponding to the saturation region and an output signal of a pixel region corresponding to the noise region according to gain of each pixel region.

12. A method of generating an X-ray image, the method comprising:
    generating and radiating X-rays to a subject;
    detecting and converting X-rays transmitted through the subject into an image signal by an X-ray detector including a plurality of detection regions, wherein each of the detection regions includes at least one pixel region;
    analyzing the image signal of the subject to extract a noise region and a saturation region from the image signal; and
    setting gain of the X-ray detector for each detection region of the X-ray detector according to the extracted noise region and the saturation region.

13. The method according to claim 12, wherein the analyzing the image signal of the subject includes determining a detection region, a level of an image signal of which is equal to or greater than a first reference level, among the detection regions of the X-ray detector as the saturation region and determining a detection region, a level of an image signal of which is equal to or less than a second reference level, among the detection regions of the X-ray detector as the noise region.

14. The method according to claim 13, wherein the setting the gain of the X-ray detector according to detection regions includes setting a value higher than original gain as gain with respect to the noise region of the X-ray detector and setting a value lower than the original gain as gain with respect to the saturation region of the X-ray detector, wherein the original gain is gain of the X-ray detector applied when the analyzed image signal is obtained.

15. The method according to claim 12, further comprising setting offset according to the detection regions of the X-ray detector.

16. An X-ray detector comprising:
a light receiver configured to detect and convert X-rays into an electrical signal and include a plurality of detection regions, wherein each of the detection regions includes at least one pixel region; and
a gain control circuit to dynamically control gain of the electrical signal output by the light receiver,
wherein the gain control circuit analyzes the electrical signal to extract a noise region and a saturation region and sets the gain for each of the detection regions according to the extracted noise region and the saturation region.

17. An X-ray detector of an X-ray imaging apparatus which provides an X-ray image of a subject, the X-ray detector comprising:
a plurality of detection regions configured to detect and convert X-rays transmitted through the subject into an electrical signal, wherein each of the detection regions includes at least one pixel region and wherein
an amplifier configured to amplify a converted electrical signal of an X-ray, wherein a noise region and a saturation region of the converted electrical signal are determined based on comparison between a level of the converted electrical signal with a predetermined reference level and gain of the amplifier is determined based on the noise region and the saturation region.

18. The X-ray detector according to claim 17, wherein the gain of the amplifier is decreased when the level of the electrical signal is equal to or greater than a first reference level.

19. The X-ray detector according to claim 18, wherein the first reference level corresponds to a saturation level.

20. The X-ray detector according to claim 17, wherein the gain of the amplifier is increased when the level of the electrical signal is equal to or lower than a second reference level.

21. The X-ray detector according to claim 20, wherein the second reference level corresponds to a noise level.

22. The X-ray detector according to claim 17, wherein, based on a result of the comparison, the gain of the amplifier is determined as a value selected from among a plurality of values pre-mapped to respective intensity levels.

23. The X-ray detector according to claim 22, wherein the plurality of values are pre-mapped to the respective intensity levels by simulating intensity of X-rays according to at least one from among a thickness and a density of the subject.

24. An X-ray imaging apparatus comprising:
an X-ray source;
an X-ray detector including a plurality of detection regions and configured to detect an X-ray intensity of an X-ray passing through a subject; and
a controller configured to control gain of the X-ray detector based on the detected X-ray intensity according to each of the plurality of detection regions,
wherein the controller analyzes the detected X-ray intensity to extract a noise region and a saturation region and sets the gain of the X-ray detector for each of detection regions of the X-ray detector according to the extracted noise region and the saturation region.

25. The X-ray imaging apparatus according to claim 24, wherein the controller controls the gain of the X-ray detector based on at least one from among a plurality of values pre-mapped to respective intensity levels.

26. The X-ray imaging apparatus according to claim 24, wherein the plurality of values are pre-mapped to the respective intensity levels by simulating intensity of X-rays according to at least one from among a thickness and a density of the subject.

27. The X-ray imaging apparatus according to claim 24, wherein, when the controller obtains an X-ray image of the subject by using the controlled gain of the X-ray detector, the controller processes the X-ray image to correspond to substantially uniform gain among the plurality of detection regions.

* * * * *